United States Patent
Kato (10) Patent No.: US 8,041,323 B2
(45) Date of Patent: Oct. 18, 2011

(54) PORTABLE ELECTRONIC UNIT

(75) Inventor: Kazuo Kato, Chiba (JP)

(73) Assignee: Seiko Instruments Inc. (JP)

( * ) Notice: Subject to any disclaimer, the term of this patent is extended or adjusted under 35 U.S.C. 154(b) by 1480 days.

(21) Appl. No.: 11/488,251

(22) Filed: Jul. 18, 2006

(65) Prior Publication Data

US 2007/0046372 A1    Mar. 1, 2007

(30) Foreign Application Priority Data

Jul. 21, 2005   (JP) .................................. 2005-210870

(51) Int. Cl.
*H04B 1/06* (2006.01)
*H04K 3/00* (2006.01)

(52) U.S. Cl. .................................. 455/235.1; 455/240.1

(58) Field of Classification Search ...... 455/232.1–253.2
See application file for complete search history.

(56) References Cited

U.S. PATENT DOCUMENTS

| | | | | |
|---|---|---|---|---|
| 5,001,776 A | * | 3/1991 | Clark | 455/226.2 |
| 6,215,987 B1 | * | 4/2001 | Fujita | 455/127.3 |
| 6,580,905 B1 | * | 6/2003 | Naidu et al. | 455/522 |
| 7,319,363 B2 | * | 1/2008 | Langenbach et al. | 330/279 |
| 2003/0073911 A1 | | 4/2003 | Yoshimura et al. | |
| 2006/0041200 A1 | | 2/2006 | Dotter et al. | |

FOREIGN PATENT DOCUMENTS

| | | |
|---|---|---|
| EP | 1402817 A1 | 3/2004 |
| GB | 2262347 A | 6/1993 |
| JP | 05218868 | 8/1993 |
| JP | 07273699 | 10/1995 |
| JP | 09116453 | 5/1997 |
| JP | 2002143110 | 5/2002 |
| WO | WO-2004/098405 A1 | 11/2004 |

* cited by examiner

*Primary Examiner* — Lee Nguyen
(74) *Attorney, Agent, or Firm* — Adams & Wilks (57) ABSTRACT

A portable electronic unit has a transmission-side section that transmits a signal and a receiving-side section that receives a signal from the transmission-side section. The receiving-side section includes a gain control amplification device that amplifies and outputs a signal from the transmission-side section. The gain control amplification device has a first amplification circuit that amplifies and outputs a signal from the transmission-side section, a detection circuit that detects and outputs a signal from the first amplification circuit, a gain control amplification circuit that amplifies and outputs a signal from the detection circuit, and a gain control circuit that controls a gain in the gain control amplification circuit in response to a level of a signal from the detection circuit.

7 Claims, 5 Drawing Sheets

PORTABLE ELECTRONIC UNIT

BACKGROUND OF THE INVENTION

1. Field of the Invention

The present invention relates generally to portable electronic units and, more specifically, to a portable electronic unit having transmission-side means for transmitting a signal and receiving-side means for receiving a signal from the transmission-side means, at least one of which is carried and used by a user, and to a portable electronic unit used as a portable biological information measurement unit such as a heart rate meter for measuring biological information such as a heart beat, for example.

2. Description of the Prior Art

Conventionally, portable biological information measurement apparatuses have been developed for measuring human biological information about heart beats, pulses, and the number of steps taken. The portable biological information measurement apparatus typically has transmission-side means for detecting and wirelessly transmitting biological information about a user and receiving-side means for receiving and reporting biological information from the transmission-side means. A user of the portable biological information measurement apparatus carries and uses at least one of the transmission-side means and receiving-side means thereof.

For example, a portable heart rate measurement apparatus has been developed, which is a kind of a portable biological information measurement apparatus. The heart rate meter itself for detecting a heart beat and wirelessly transmitting heart rate information is pressed and attached to the chest of the user with a chest belt. A wristwatch type unit is used, which has a receiving portion and a reporting portion. Heart rate information from the heart rate meter is received by the receiving portion of the wristwatch type unit and reported by the reporting portion thereof.

The receiving portion typically includes an antenna for converting an electric wave signal received from the heart rate meter into voltage, a high-frequency amplification circuit for amplifying a miniature voltage generated at the antenna, a detection circuit for detecting an amplified signal, a low-frequency amplification circuit and a comparator for demodulating heart rate data. The configuration described above allows the user to know heart rate information detected by the heart rate meter using the wristwatch type unit located away from the heart rate meter itself.

If an electric wave is radiated from a miniature dipole antenna, the electric field strength $E\theta$ at a point a distance r away from the antenna is expressed by the following equation:

$$E_\theta = j \cdot (60\pi l/\lambda) \cdot I e^{(-j\beta r)} \cdot (1/r + 1/(j\beta r^2) + 1/((j\beta)^2 r^3))$$

If, for example, a long wave signal with a signal frequency of about 100 kHz is used, in short-range communications within 1 m or less, a change in electric field strength reaches about 30 dB in a range of 10 cm to 100 cm and increases to 60 dB, another 30 dB up in a range of 1 to 10 cm. To allow data receipt at a distance of 1 m, a receiving circuit requires an amplification degree of at least 60 dB. A change in a communication distance between the transmission side and the receiving side from 1 cm to 1 m will result in a change in input voltage of 60 dB or so at the receiving side.

Meanwhile, a large number of battery-powered portable units cannot take a dynamic range because these portable units have a low source voltage of 2 to 3V. For a receiving circuit with a fixed gain, a change in data pulse width will therefore result, which may cause a problem that a digital signal cannot be demodulated accurately during short-range communications.

To solve the problem described above, a method is commonly used in which a gain control amplification circuit is used in a receiving circuit.

In the invention described in Non-Patent Document 1. a high-frequency amplification circuit is composed of a transistor-based gain control amplification circuit. A gain is controlled by controlling a collector current (or emitter current) of the transistor.

This allows the construction of a gain control amplification circuit having a relatively simple configuration. However, such a gain control amplification circuit requires a large collector current (e.g., 0.5 to 2 mA), thus resulting in problematic large power consumption. The use of a transformer in the high-frequency amplification circuit also makes it problematically difficult to reduce the size of such a circuit, for example.

In an automatic gain control unit described in Patent Document 2, the control amplifier is controlled using an automatic gain control section that uses an output signal from a mixer, i. e., a signal from the upstream side of the intermediate-frequency filter. The automatic gain control section includes a particular weighting filter, which is connected to the output side of the mixer to output a control signal for a control amplifier for gain control through a detector. The detector is an average-value or peak-value rectifier that includes a diode and a capacitor connected to the downstream side thereof.

The configuration described above allows gain control. Besides a detection circuit for signals received, however, a separate detection circuit for gain control is required, which problematically makes the configuration of the unit complicated and the unit expensive.

In addition, the high-frequency amplification circuit will require gain control. The use of the same circuit configuration as described in the above-mentioned Non-Patent Document 1 will therefore raise problems as described above, such as larger consumption.

<Non-Patent Document 1> Transistor Technology, published by CQ Publishing Co., Ltd., Vol. 350. page 351. October 1998

<Patent Document 2> JP-T-2005-513903. paragraphs (0011) to (0019), FIG. 1

The present invention contemplates eliminating the problems described above. An object of the invention is to provide a portable electronic unit that consumes less power. Another object of the invention is to provide a portable electronic unit that has a smaller size.

SUMMARY OF THE INVENTION

The present invention provides a portable electronic unit comprising transmission-side means for transmitting a signal, and receiving-side means for receiving a signal from the transmission-side means in which at least one of the transmission-side means and the receiving-side means is carried and used by a user; characterized in that the receiving-side means has gain control amplification means for amplifying and outputting a signal from the transmission-side means, and the gain control amplification means includes a first amplification circuit for amplifying and outputting a signal from the transmission-side means, a detection circuit for detecting and outputting a signal from the first amplification circuit, a gain control amplification circuit for amplifying and outputting a signal from the detection circuit, and a gain control circuit for controlling a gain in the gain control amplification circuit in response to a level of a signal from the detection circuit.

The first amplification circuit in the gain control amplification circuit amplifies and outputs a signal from the transmission-side means. The detection circuit detects and outputs a signal from the first amplification circuit. The gain control circuit controls a gain in the gain control amplification circuit in response to a level of the signal from the detection circuit. The gain control amplification circuit amplifies and outputs a signal from the detection circuit with a gain controlled by the gain control circuit.

The receiving-side means may be configured to have setup means for controlling the gain control circuit so that the gain control circuit brings a gain in the gain control amplification circuit to a predetermined value when a power supply is turned on.

The setup means may also be configured to control the gain control circuit so that the gain control circuit maximizes a gain in the gain control amplification circuit.

The gain control amplification circuit may also be configured to have a second amplification circuit for amplifying and outputting a signal from the detection circuit and a feedback circuit for feeding an output from the second amplification circuit back to an input side of the second amplification circuit and the gain control circuit may be configured to control a gain in the gain control amplification circuit by controlling an amount of feedback from the feedback circuit.

The feedback circuit may also be configured to have an impedance circuit connected between an output portion and an input portion of the second amplification circuit and the gain control circuit may be configured to control the amount of feedback by controlling an impedance value for the impedance circuit.

The impedance circuit may also be configured to have a plurality of resistors and comprise a switch connected in parallel to any of the plurality of resistors and the gain control circuit may be configured to control a gain in the gain control amplification circuit stepwise by opening and closing the switch for controlling purposes to control the amount of feedback stepwise.

The gain control circuit may also be configured to control the amount of feedback by opening and closing the switch for controlling purposes in response to the control of the setup means when the power is turned on and control a gain of the gain control amplification circuit to a predetermined value.

The receiving-side means may also be configured to have power control means that actuates a power supply for the gain control amplification means at a predetermined cycle.

The transmission-side means may also be configured to transmit a signal to the receiving-side means by means of electromagnetic induction.

The transmission-side means may also be configured to have biological information detection means for detecting biological information and biological information transmission means for wirelessly transmitting a digital signal indicative of biological information detected by the biological information detection means and the receiving-side means may be configured to further have digital signal output means for outputting a signal from the gain control amplification means as a digital signal and reporting means for reporting biological information based on a digital signal from the digital signal output means.

The biological information detection means in the transmission-side means may be configured to detect a heart beat, pulsation or a walk while the biological information transmission means may be configured to transmit biological information about a heart rate, a pulse rate or the number of steps taken as the digital signal and the reporting means may be configured to report the heart rate, pulse rate or the accumulated number of steps taken as biological information.

BRIEF DESCRIPTION OF THE SEVERAL VIEWS OF THE DRAWINGS

A preferred form of the present invention is illustrated in the accompanying drawings in which.

DETAILED DESCRIPTION OF THE PREFERRED EMBODIMENTS

A portable electronic unit according to an embodiment of the invention will be described below. Note that in this embodiment, an example of a portable biological information measurement apparatus will be described as a portable electronic unit and that an example of a heart rate meter will be described below, which is a kind of the portable biological information measurement apparatus.

Figure 1:
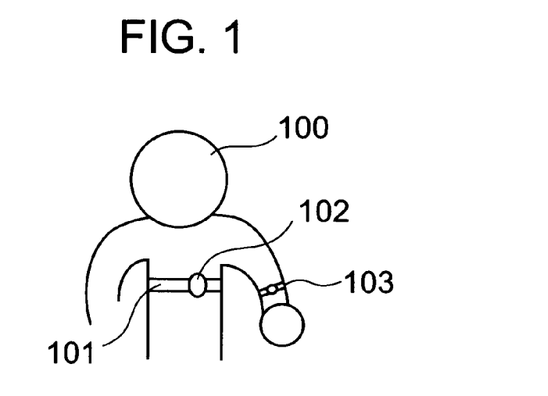
FIG. 1 is a diagram showing an aspect of use of a heart rate meter, which is a portable electronic unit according to an embodiment of the present invention.

FIG. 1 shows an aspect of the use of a heart rate meter, which is a portable electronic unit according to an embodiment of the present invention.

In FIG. 1, a portable heart rate meter has a heart beat detection section 102 and a heart beat reporting section 103. A chest belt 101 into which the heart beat detection section 102 is integrated is attached to the chest of a heart rate meter user 100, whose heart beat is measured, so that the section 102 comes into contact with the skin. The heart beat reporting section 103 is also attached to the arm of the user 100, which looks like a wrist watch and has wrist watch functions. The heart beat detection section 102 and the heart beat reporting section 103 are configured to allow wireless signal transmission and reception (e.g., by means of electromagnetic induction).

The detailed operation of the heart rate meter will described later. The heart beat detection section 102 detects heart beats and transmits a heart rate/unit time as heart rate information to the heart beat reporting section 103. The heart beat reporting section 103 then receives the heart rate information by means of electromagnetic induction and performs reporting operations such as displaying the heart rate.

Note that the heart beat detection section 102 constitutes transmission-side means while the heart beat reporting section 103 constitutes receiving-side means.

Figure 2:
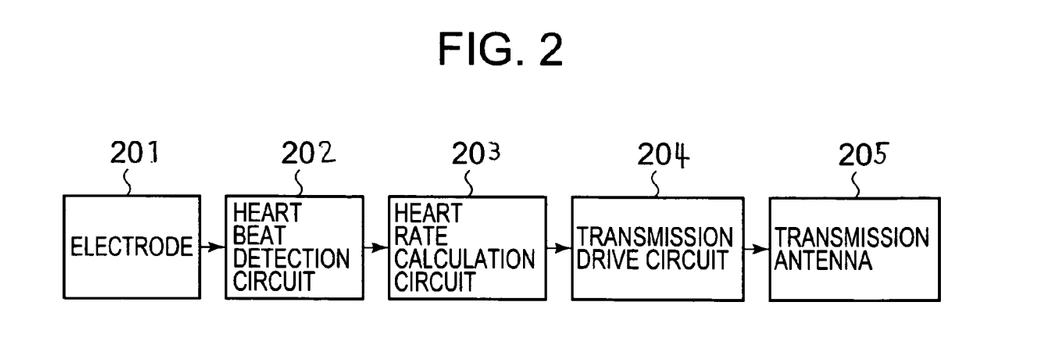
FIG. 2 is a block diagram of a heart beat detection section used for the embodiment of the present invention.

FIG. 2 is a block diagram of the heart beat detection section 102 shown in FIG. 1. In FIG. 2, heart beat detection section 102 has an electrode 201 for detecting a heart beat and outputting a detection signal corresponding to a heart beat, a heart beat detection circuit 202 for converting and outputting a detection signal from the electrode 201 into a rectangular wave, a heart rate calculation circuit 203 for calculating a heart rate per unit time based on a signal from the heart beat detection circuit 202 and outputting the heart rate information in the form of a digital signal, a transmission antenna 205, and a transmission drive circuit 204 for converting and transmitting the heart rate information into a signal (for example, a burst signal) transmittable through the transmission antenna 205 by means of electromagnetic induction. The electrode 201 and the heart beat detection circuit 202 together constitutes a biological information detection means while the heart rate calculation circuit 203, the transmission drive circuit 204 and the transmission antenna 205 together constitutes biological information transmission means.

Figure 3:
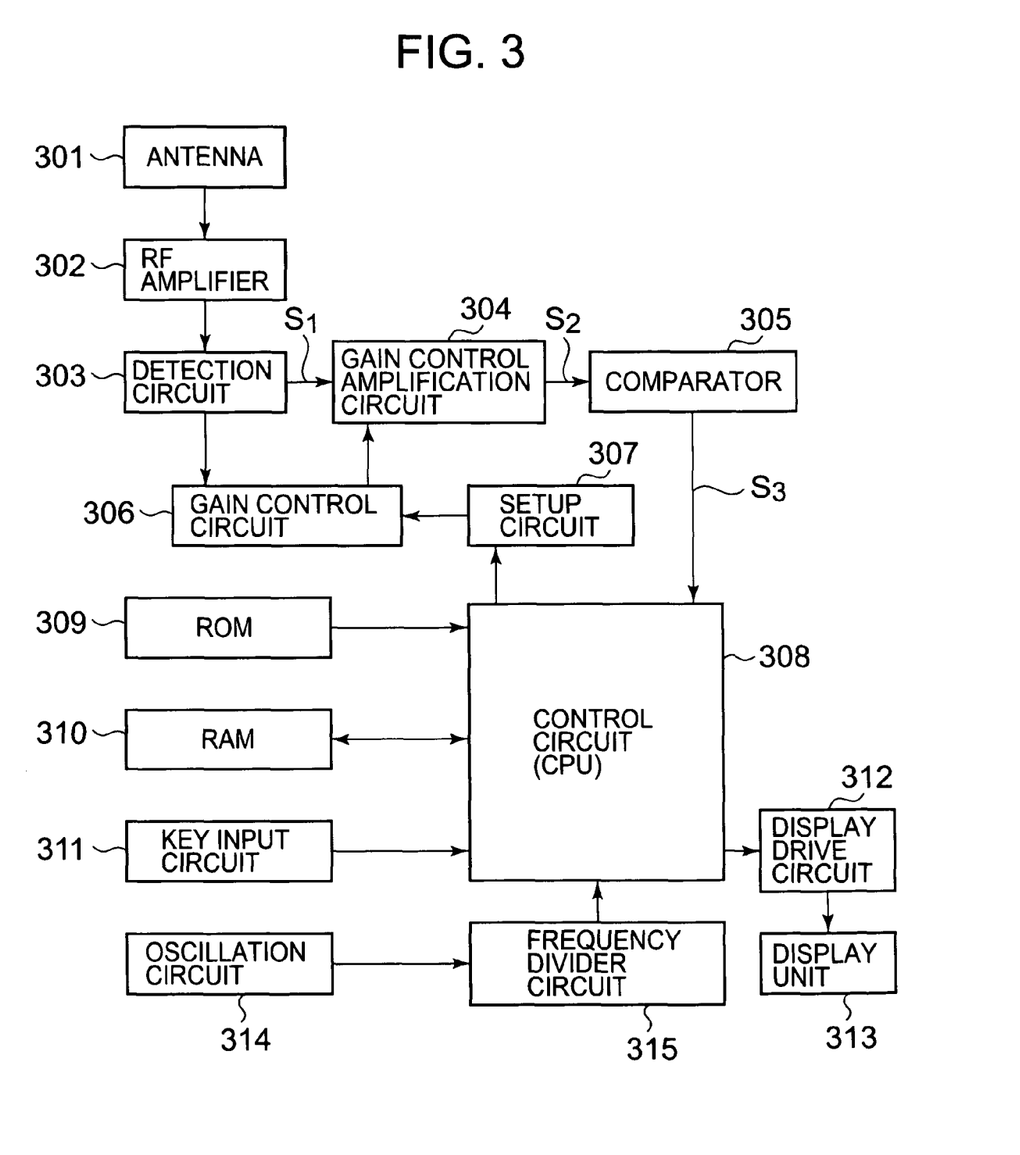
FIG. 3 is a block diagram of a reporting section used for the embodiment of the present invention.

FIG. 3 is a block diagram of the heart beat reporting section 103 shown in FIG. 1. In FIG. 3, the reporting section 103 has an antenna 301 for receiving heart rate information from the heart beat detection section 102 by means of electromagnetic induction, a high-frequency amplification circuit 302 (RF amplifier) as a first amplification circuit for amplifying the heart rate information received by the antenna 301, a detection circuit 303 for detecting an output signal of the high-frequency amplification circuit 302, a gain control amplification circuit 304 capable of changing a gain for amplifying an output signal of the detection circuit 303, a comparator 305 as digital signal output means for comparing an output signal of the gain control amplification circuit 304 with a predetermined reference signal for waveform formation and outputting the output signal as a digital signal, a gain control circuit 306 for controlling a gain in the gain control amplification circuit 304 to a gain responsive to the level of the output signal of the detection circuit 303, a setup circuit 307 for controlling the gain control circuit 306 so that a gain in the gain control amplification circuit 304 is brought to a predetermined value (a maximum value in the embodiment) when a power supply is turned on, a control circuit 308 composed of a central processing unit (CPU), a read-only memory (ROM) 309 having a program and the like executed by the control circuit 308 stored therein in advance, a random access memory (RAM) 310 for storing various data such as heart rate data and the like, a key input circuit 311 as operating means, a display drive circuit 312, a display unit 313 as reporting means for displaying a heart rate, time of day and the like, an oscillation circuit 314 for generating a signal for a predetermined frequency, and a frequency divider circuit 315 for dividing the frequency of an output signal of the oscillation circuit 314 and generating a time signal that will serve as a reference for an timing operation.

The high-frequency amplification circuit 302, the detection circuit 303, the gain control amplification circuit 304, and the gain control circuit 306 together constitute gain control amplification means. In addition, the setup circuit 307 and the control circuit 308 together constitutes setup means.

Figure 4:
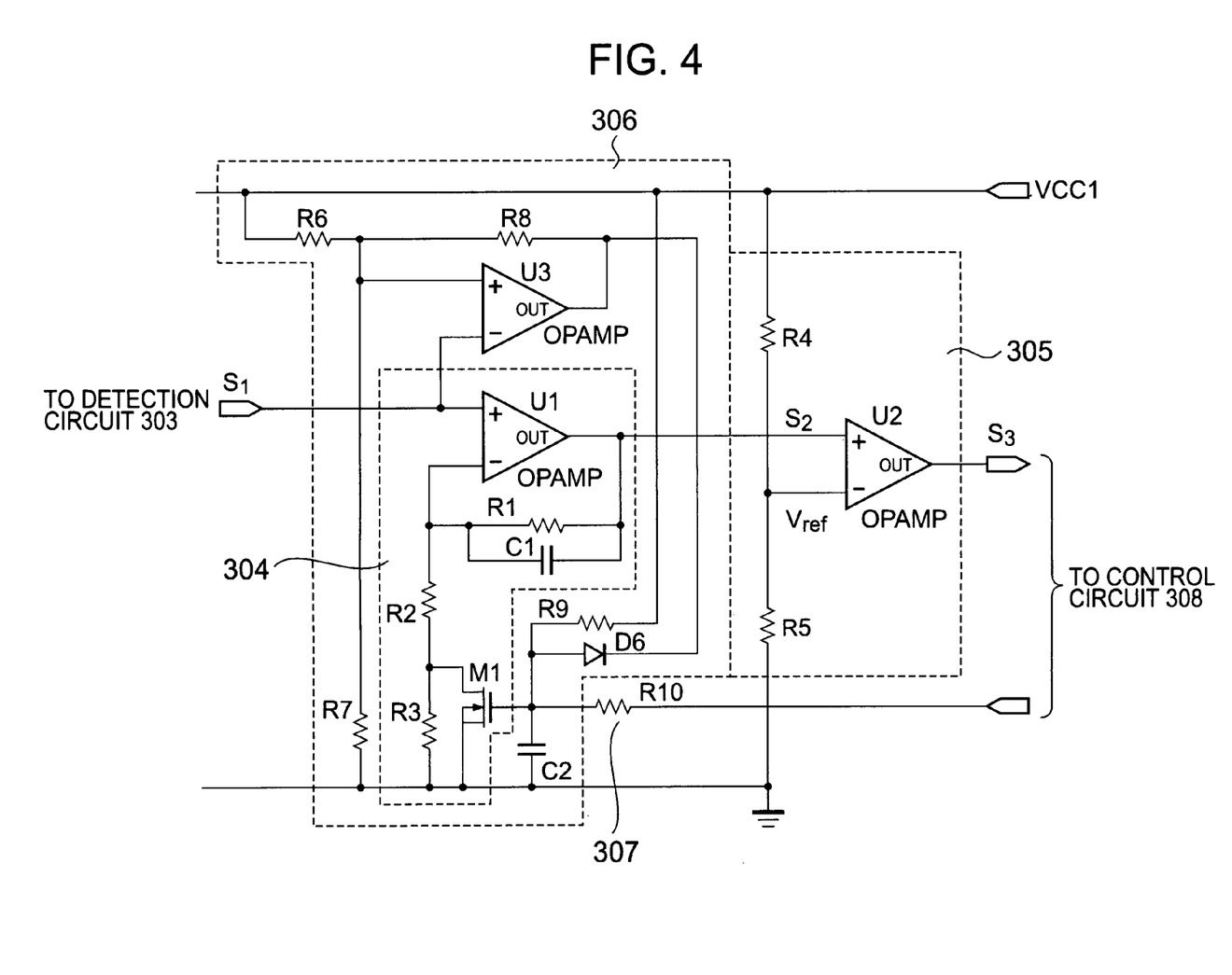
FIG. 4 is a detailed circuit diagram of components in the embodiment of the present invention.

FIG. 4 is a circuit diagram showing the details of the gain control amplification circuit 304, the comparator 305, the gain control circuit 306, and the setup circuit 307. The parts in FIG. 4 same as in FIG. 3 have the same symbols.

In FIG. 4, the gain control amplification circuit 304 has a low-frequency amplification circuit U1 as a second amplification circuit. The gain control amplification circuit 304 also has a plurality of resistors R1 to R3 connected in series to one another between one input portion (the negative input portion) and the output of the amplification circuit U1, a capacitor C1 connected in parallel to the resistor R1, an electric-field-effect transistor (FET) M1 connected in parallel to the resistor R3 and constituting a switch. A signal from the detection circuit 303 is inputted into the other input portion of the amplification circuit U1.

The resistors R1 to R3, the capacitor C1 and the switch M1 together constitutes a feedback circuit. In addition, the resistors R1 to R3 and the capacitor C1 together constitutes an impedance circuit.

If the gate potential for the transistor M1 is at a high level, the transistor M1 turns on (the switch is closed) and a short circuit results between the both ends of the resistor 3, thus resulting in a smaller amount of feedback. The gain in the gain control amplification circuit 304 therefore reaches a predetermined large value (maximum value). If the gate potential for the transistor M1 is at a low level, the transistor M1 turns off (the switch is opened) and the opposite ends of the resistor R3 open, thus resulting in a larger amount of feedback. The gain in the gain control amplification circuit 304 therefore decreases to a predetermined small value (minimum value). As described above, the gain in the gain control amplification circuit 304 is controlled not to change continuously but to change stepwise (in two steps in the embodiment).

The gain control circuit 306 has an amplification circuit U3, a plurality of resistors R6 to R9, a capacitor C2, and a diode D6. A signal from the detection circuit 303 is inputted into one input portion (negative input portion) of the amplification circuit U3. While a signal at or below a predetermined level is inputted to the gain control circuit 306 from the detection circuit 303, the gain control circuit 306 functions to control the cathode of the diode D6 to a high level to open both ends of the capacitor C2. If a signal above the predetermined level is inputted to the circuit 306 from the detection circuit 303, the gain control circuit 306 functions to control the cathode of the diode D6 to a low level to short both ends of the capacitor C2.

The comparator 305 has a plurality of resistors R4, R5 for producing a reference potential and an amplification circuit U2. The connecting point (reference potential point) between the resistors R4 and R5 is connected to one input portion (negative input portion) of the amplification circuit U2. A signal from the gain control amplification circuit 304 is inputted to the other input portion. If a signal from the gain control amplification circuit 304 is above a predetermined reference potential level, the comparator 305 outputs a high-level signal. If a signal from the gain control amplification circuit 304 is at or below a predetermined reference potential level, the comparator 305 outputs a low-level signal. As described above, the comparator 305 converts a signal from the gain control amplification circuit 304 into two values for output as a digital signal.

The resistor R10 is a resistor that constitutes the setup circuit 307. The resistor R10 is provided to control the gain control circuit 306 so that the circuit 306 brings the gain in the gain control amplification circuit 304 to a predetermined value (a maximum value, in the embodiment) when the power supply for the gain control amplification circuit is turned on. When the power supply for the gain control amplification circuit is turned on, the control circuit 308 feeds a high-level signal to the resistor R10. This forces the capacitor C2 to rapidly get charged and control the transistor M1 to be on so that the gain in the gain control amplification circuit 304 is at the maximum value directly after the power supply is turned on.

Figure 5:
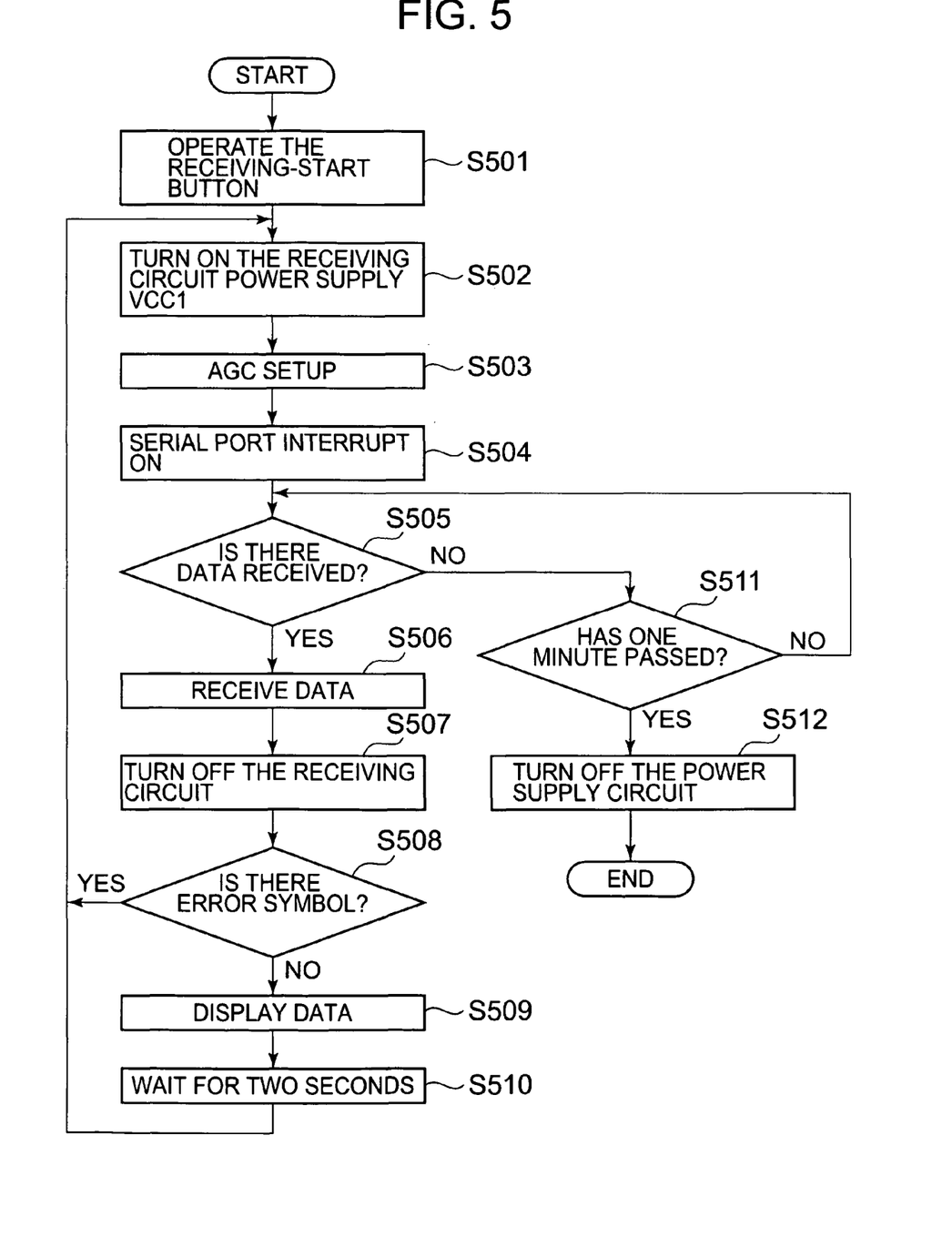
FIG. 5 is a flow chart showing processing in the embodiment of the present invention.

FIG. 5 is a flow chart showing the operation of a heart rate meter, which is a portable electronic unit according to an embodiment of the investigation. The flow chart mainly shows a processing performed by executing a program the control circuit 308 has pre-stored in a ROM 309.

Figure 6A:
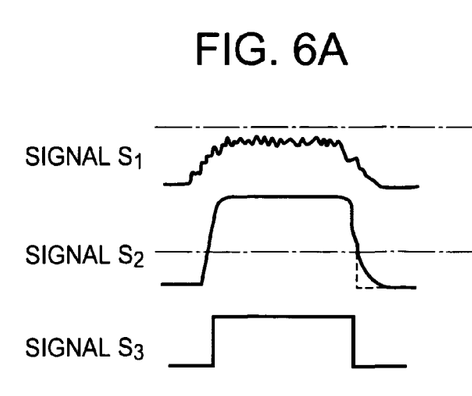
FIGS. 6A and 6B are signal waveform diagrams for describing the operation of the embodiment of the present invention.
Figure 6B:
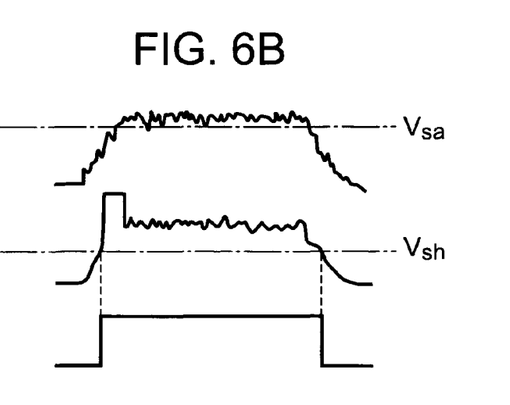

FIG. 6 is a signal waveform diagram for describing the operation of a heart rate meter, which is a portable electronic unit according to an embodiment of the invention. FIG. 6 shows a relationship between an output signal S1 of a detection circuit 303, an output signal S2 of a gain control amplification circuit 304 and an output signal S3 of a comparator 305 in case a gain control amplification circuit 304 is gain controlled by a gain control circuit 306 and in case it is not.

In FIG. 6, FIG. 6A of the signal waveform diagram covers a distance between a heart beat detection section 102 and a reporting section 103 which is longer than predetermined. In other words, FIG. 6A covers a gain control amplification circuit 304 without gain control by a gain control circuit 306. FIG. 6B of the signal waveform diagram covers a distance between a heart beat detection section 102 and a reporting section 103 which is shorter than predetermined. In other words, FIG. 6B covers a gain control amplification circuit 304 with gain control by a gain control circuit 306.

As shown at FIG. 6A, if the output signal S1 from the detection circuit 303 is at or below a gain control threshold value Vsa, which serves as a criterion about whether to control a gain or not, the gain control circuit 306 outputs a high-level output signal, thus making the cathode of the diode D6 at a high level. The capacitor C2 is therefore kept charged through the setup circuit 307 and the transistor M1 is kept on (closed). The gain in the gain control amplification circuit 304 is not controlled by the gain control circuit 306 and the gain control amplification circuit 304 performs amplification operation with a large gain. The comparator 305 then converts the output signal S2 of the gain control amplification circuit 304 into a waveform with a waveform formation threshold Vsh for output to the control circuit 308 as a digital signal S3.

As shown at FIG. 6B, if, on the other hand, the output signal S1 from the detection circuit 303 is above a gain control threshold value Vsa, the gain control circuit 306 outputs a low-level output signal, thus making the cathode of the diode D6 at a low level. The. capacitor C2 is therefore discharged and the transistor M1 is kept off (opened). The gain in the gain control amplification circuit 304 is then controlled by the gain control circuit 306 and the gain control amplification circuit 304 performs amplification operation with a small gain. The comparator 305 then converts the output signal S2 of the gain control amplification circuit 304 into a waveform with a waveform formation threshold Vsh for output to the control circuit 308 as a digital signal S3.

Figure 7:
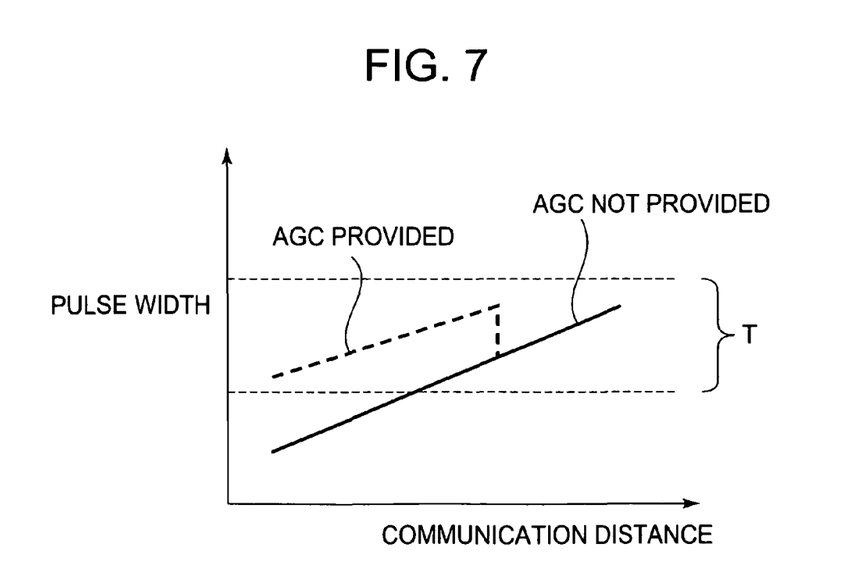
FIG. 7 is an explanatory diagram for describing the operation of the embodiment of the present invention.

FIG. 7 is an explanatory diagram for describing the operation of a heart rate meter, which is a portable electronic unit according to an embodiment of the invention. FIG. 7 shows how a range available for normal communications between the heart beat detection section 102 and the reporting section 103 increases because of a gain in the gain control amplification circuit 304 by the gain control circuit 306.

As shown in FIG. 7, if a gain in the gain control amplification circuit 304 is not controlled by the gain control circuit 306, the pulse width of the digital signal S3 outputted from the comparator 305 changes as shown by the solid line according to the distance between the heart beat detection section 102 and the reporting section 103. A range of distance where the pulse width falls within the receivable range T is therefore relatively small. In the embodiment, however, a gain in the gain control amplification circuit 304 is controlled stepwise by the gain control circuit 306. Thus, the pulse width of the digital signal S3 outputted from the comparator 305 increases. The range of distance where the pulse width falls within the receivable range T is therefore relatively wide.

The operation of the embodiment of the present invention will be described in detail with reference to FIGS. 1 to 7.

If a user 100 does not perform any operation on the reporting section 103, the reporting section 103 functions as a timepiece. In other words, if the reporting section 103 functions as a timepiece, an oscillation circuit 314 produces a reference signal and a frequency divider circuit 315 produces a time signal that serves as a reference for time measurement by dividing the frequency of the reference signal. A control circuit 308 counts the time signal for timing operation and controls a display drive circuit 312 to thereby display time information such as a current time of the day on a display unit 313.

In case of heart beat measurement, the user 100 of a heart rate meter operates the heart beat detection section 102 and attaches the heart beat detection section 102 to the chest of the user with a chest belt 101, as shown in FIG. 1. The user also attaches the reporting section 103 to the arm of the user.

Under this condition, the user operates a receipt-starting button contained in a key input circuit 311 to start the operation of the reporting section 103.

When detecting that the receipt-starting button has been operated (step S501), the control circuit 308 feeds electric power to (Vcc 1) and starts a receiving circuit contained in the reporting section 103 (step S502). The control circuit 308 then functions as power control means.

The receiving circuit is a circuit required for receiving a signal from the heart beat detection section 102 and gain control amplification means corresponds to that circuit in the embodiment. Note that a circuit element of gain control amplification means that consumes large power, for example, a high-frequency amplification circuit 302 may be configured to start the power supply as a receiving circuit.

The control circuit 308 then starts the power supply for the gain control amplification means. At the same time, the control circuit 308 feeds a high-level signal to a resistor R10 to perform a setup so that a gain in the gain control amplification circuit 304 is brought to a maximum value (step S503).

In other words, the control circuit 308 feeds a high-level setup signal to a capacitor C2 through the resistor R10, thus forcing the capacitor C2 to be charged rapidly. When the voltage of the capacitor C2 is above a predetermined level, the control circuit 308 controls a transistor M1 to be on (i.e., the resistor R3 is shorted) and controls the gain control circuit 306 so that a gain in the gain control amplification circuit 304 is brought to a maximum value.

In this way, the gain control amplification circuit 304 amplifies a detection signal S1 from a detection circuit 303 with a gain (a high gain in this case) specified by the gain control circuit 306 and outputs the signal to the comparator 305. The comparator 305 converts a signal from the gain control amplification circuit 304 into two values for output to the control circuit 308.

Note that if an output signal S1 from a detection circuit 303 is at or below a gain control threshold Vsa (i.e., in case of remote communications) as shown in FIG. 6, the comparator U3 in the gain control circuit 306 outputs a high-level output signal and the cathode of the diode D6 is at a high level, thus keeping the gain in the gain control amplification circuit 304 high.

If, however, the output signal S1 from the detection circuit 303 is above the gain control threshold Vsa (i.e., in case of short-range communications), the comparator U3 in the gain control circuit 306 outputs a low-level output signal and the cathode of the diode D6 is at a low level, thus discharging the capacitor C2 with a drop in capacitor C2 terminal voltage. When the terminal voltage of the capacitor C2 is at or below a predetermined value, the transistor M1 is turned off and the gain in the gain control amplification circuit 304 is switched to a low value.

As described above, the pulse width for the digital signal S3 outputted from the comparator 305 falls within a receivable range T as shown in FIG. 7, thus providing an accurate data receiving operation.

The control circuit 308 then performs interrupt processing (step S504) and determines if there is data received, that is, if a digital signal has been received from the comparator 304 (step S505).

If the control circuit 308 determines that there is data received at step S505, the control circuit 308 receives a digital signal from the comparator 305 and loads heart rate data thereinto (step S506) before shutting off the power of the receiving circuit (step S507).

The control circuit 308 then determines if there is an error symbol in data received, that is, if the data received is in a correct form (step S508).

If the control circuit 308 determined, at step S508, that the data received is in a correct form, the control circuit 308 stores the data in an RAM 310 and outputs the data to a display drive circuit 312 for reporting processing for the data (step S509). The display drive circuit 312 is then driven so that the display unit 313 displays the data for reporting purposes.

If the control circuit 308 determined, at step S508, that the data received is not a signal in a correct form, that is, the data received is not a regular signal, the control circuit 308 returns to step S502 without performing reporting processing.

If the control circuit 308 determines, at step S505, that there is no data received, the control circuit 308 determines if a predetermined time (one minute in the embodiment) has passed (step S511). If the predetermined time has not passed, the control circuit 308 returns to step S505. If the predetermined time has passed, the control circuit 308 turns off the receiving circuit and ends the processing (step S512).

The control circuit 308 then performs a processing for reporting the heart rate data. After waiting for a predetermined time (two seconds in the embodiment), the control circuit 308 returns to step S502 to repeat the processing described above (step S510). As described above, the control circuit 308 functions as power control means and turns on the receiving circuit (gain control amplification means in the embodiment) at a predetermined cycle to repeat the processing described above. In this way, the control circuit 308 reports heart rate information about the user 100 to the user 100 on the display unit 313.

Display switching through the operation of the key input circuit 311 makes it possible to select and display various displays, such as a biological information display displaying information such as heart rate information and a current time, on the display unit 313.

As described above, according to the embodiment, the gain control amplification circuit 304 is provided behind the high-frequency amplification circuit 302 and the detection circuit 303 to configure a circuit using a low-frequency amplification circuit. This eliminates the necessity of employing a configuration that performs gain control through the control of transistor collector current, thus allowing a reduction in current and therefore power consumption control.

The embodiment of the present invention eliminates the need for gain control at a high-frequency amplification circuit, which eliminates the need for the use of circuit wiring considering the effect of stray capacity of a high-frequency signal and the use of a transformer for a high-frequency circuit. This allows a reduction in the size of the portable electronic unit, as small as a wrist watch, and the stable operation of the unit. It also provides designing improvements.

In addition, gain control according to the embodiment is simple control, which is not linear but stepwise such transistor M1 on and off (two steps in the embodiment). The simplicity of gain control allows a reduction in the number of parts for the gain control circuit 306 and simple and inexpensive configuration of the unit.

The setup circuit 307 for quickly setting up the gain control circuit 306 is provided for the intermittent actuation of the receiving circuit for less power consumption. This provides the effect of allowing the quick setup of the gain control circuit 306 to a predetermined gain (a high gain in the embodiment).

Note that in the embodiment, communications between the heart beat detection section 102 and reporting section 103 is performed by means of electromagnetic induction. The communications may be performed not only by means of electromagnetic induction but wirelessly, such as using electric waves and light.

An example of a portable electronic unit that handles biological information has been described. It is also possible to apply the embodiment to a portable electronic unit handling other information.

In the example described above, both of the heart beat detection section 102 and the reporting section 103 are attached to the body of the user 100 to carry and use these sections. Various changes can be made to these sections depending on the type of a portable electronic unit of interest. For example, the user can place these sections in his bag to carry and use them.

The example of a heart rate meter that handles heart beats as biological information has been described. However, other types of biological information may be used. The transmission-side means may detect pulsation or walk as biological information. In this case, the transmission-side means can be provided with a pulsation detection section or walk detection section to transmit the pulse rate or the number of steps taken per unit time as a digital signal indicative of biological information. For the receiving-side means, the pulse rate or the accumulated number of steps taken can be reported to the user as biological information.

In the configuration described above, the display unit 313 is used as visual reporting means. A loudspeaker may be used as acoustic reporting means.

The present invention allows a reduction in consumption power. The investigation also allows a reduction in the size of a portable electronic unit.

The present invention can be applied to various types of portable electronic units with at least one of the transmission-side means and receiving-side means carried and used by a user, including biological information measurement units, such as not only a heart rate meter, a pulse meter, a pedometer, for measuring biological information such as the human's heart beat, pulsation, and walk.

What is claimed is:

1. A portable electronic unit comprising:
    transmission-side means for transmitting a signal; and
    receiving-side means for receiving the signal from the transmission-side means, the receiving-side means comprising gain control amplification means for amplifying and outputting the signal from the transmission-side means, the gain control amplification means including a first amplification circuit that amplifies and outputs the signal from the transmission-side means, a detection circuit that detects and outputs a signal from the first amplification circuit, a reverse gain control amplification circuit that amplifies and outputs the signal from the detection circuit, the reverse gain control amplification circuit having a second amplification circuit that amplifies and outputs the signal from the detection circuit and a feedback circuit for feeding an output from the second amplification circuit back to an input side of the second amplification circuit, and a gain control circuit that controls a gain in the reverse gain control amplification circuit in response to a level of the signal from the detection circuit, the gain control circuit controlling a gain in the reverse gain control amplification circuit by controlling an amount of feedback from the feedback circuit.

2. A portable electronic unit according to claim 1; wherein the feedback circuit comprises an impedance circuit connected between an output portion and an input portion of the second amplification circuit; and wherein the gain control circuit controls the amount of feedback by controlling an impedance value for the impedance circuit.

3. A portable electronic unit according to claim 2; wherein the impedance circuit has a plurality of resistors and comprises a switch connected in parallel to any of the plurality of resistors; and wherein the gain control circuit controls a gain in the reverse gain control amplification circuit stepwise by opening and closing the switch to control the amount of feedback stepwise.

4. A portable electronic unit according to claim 3; wherein the gain control circuit controls the amount of feedback by opening and closing the switch in response to the control of the setup means when the power is turned on and controls a gain of the reverse gain control amplification circuit to a predetermined value.

5. A portable electronic unit comprising:
transmission-side means for transmitting a signal; and
receiving-side means for receiving the signal from the transmission-side means, the receiving-side means comprising gain control amplification means for amplifying and outputting a the signal from the transmission-side means, the gain control amplification means including a first amplification circuit that amplifies and outputs the signal from the transmission-side means, a detection circuit that detects and outputs a signal from the first amplification circuit, a gain control amplification circuit that amplifies and outputs the signal from the detection circuit, and a gain control circuit that controls a gain in the gain control amplification circuit in response to a level of the signal from the detection circuit;
wherein the gain control amplification circuit has a second amplification circuit that amplifies and outputs the signal from the detection circuit and a feedback circuit for feeding an output from the second amplification circuit back to an input side of the second amplification circuit, the gain control circuit controlling a gain in the gain control amplification circuit by controlling an amount of feedback from the feedback circuit; and
wherein the feedback circuit comprises an impedance circuit connected between an output portion and an input portion of the second amplification circuit, the gain control circuit controlling the amount of feedback by controlling an impedance value for the impedance circuit.

6. A portable electronic unit according to claim 5; wherein the impedance circuit has a plurality of resistors and comprises a switch connected in parallel to any of the plurality of resistors; and wherein the gain control circuit controls a gain in the gain control amplification circuit stepwise by opening and closing the switch to control the amount of feedback stepwise.

7. A portable electronic unit according to claim 6; wherein the gain control circuit controls the amount of feedback by opening and closing the switch in response to the control of the setup means when the power is turned on and controls a gain of the gain control amplification circuit to a predetermined value.

* * * * *